United States Patent
Bourles et al.

(10) Patent No.: US 12,031,104 B2
(45) Date of Patent: Jul. 9, 2024

(54) METHOD FOR EXTRACTING AN OIL RICH IN POLYUNSATURATED FATTY ACIDS (PUFA)

(71) Applicant: FERMENTALG, Libourne (FR)

(72) Inventors: Louis Bourles, Bordeaux (FR); Benjamin Seguela, Libourne (FR); Emma Caderby, Cenon (FR); Hywel Griffiths, Libourne (FR)

(73) Assignee: FERMENTALG, Libourne (FR)

( * ) Notice: Subject to any disclaimer, the term of this patent is extended or adjusted under 35 U.S.C. 154(b) by 624 days.

(21) Appl. No.: 17/275,848

(22) PCT Filed: Sep. 13, 2019

(86) PCT No.: PCT/EP2019/074461
§ 371 (c)(1),
(2) Date: Mar. 12, 2021

(87) PCT Pub. No.: WO2020/053375
PCT Pub. Date: Mar. 19, 2020

(65) Prior Publication Data
US 2022/0041953 A1 Feb. 10, 2022

(30) Foreign Application Priority Data
Sep. 14, 2018 (FR) ...................... 1858293

(51) Int. Cl.
| C11B 1/10 | (2006.01) |
| A23D 9/04 | (2006.01) |
| A23L 33/12 | (2016.01) |
| A61K 8/36 | (2006.01) |
| A61K 36/02 | (2006.01) |
| C11B 3/00 | (2006.01) |

(52) U.S. Cl.
CPC .................. *C11B 1/10* (2013.01); *A23D 9/04* (2013.01); *A23L 33/12* (2016.08); *A61K 8/361* (2013.01); *A61K 36/02* (2013.01); *C11B 3/00* (2013.01); *A23V 2002/00* (2013.01); *A61K 2800/10* (2013.01)

(58) Field of Classification Search
CPC ........... C11B 1/10; C11B 1/025; C11B 3/003; A23D 9/04
See application file for complete search history.

(56) References Cited

U.S. PATENT DOCUMENTS

| 5,130,242 | A | 7/1992 | Barclay |
| 6,750,048 | B2 | 6/2004 | Ruecker et al. |
| 2005/0170479 | A1 | 8/2005 | Weaver et al. |
| 2011/0295028 | A1* | 12/2011 | Cherinko ............ C11B 3/02 554/175 |
| 2014/0323569 | A1* | 10/2014 | Raman ............... A61K 31/202 426/601 |
| 2014/0350222 | A1 | 11/2014 | Zhang et al. |
| 2015/0176042 | A1 | 6/2015 | Dennis et al. |
| 2015/0176072 | A1 | 6/2015 | Wang et al. |
| 2016/0319218 | A1 | 11/2016 | Leininger et al. |
| 2017/0016036 | A1 | 1/2017 | Calleja et al. |
| 2017/0335356 | A1 | 11/2017 | Burja et al. |

FOREIGN PATENT DOCUMENTS

| EP | 0223960 A2 | 6/1987 |
| EP | 1001034 A1 | 5/2000 |
| FR | 1186824 A | 9/1959 |
| WO | 1994/008467 A1 | 4/1994 |
| WO | 1997/037032 A2 | 10/1997 |
| WO | 2001/054510 A1 | 8/2001 |
| WO | 02/10322 A1 | 2/2002 |
| WO | 03/049832 A1 | 6/2003 |
| WO | 2010/107415 A1 | 9/2010 |
| WO | 2011/153246 A2 | 12/2011 |
| WO | 2012/035262 A1 | 3/2012 |
| WO | 2013/136025 A1 | 9/2013 |
| WO | 2013/136028 A1 | 9/2013 |
| WO | 2014/146098 A1 | 9/2014 |
| WO | 2015/004402 A2 | 1/2015 |
| WO | 2015/004403 A2 | 1/2015 |
| WO | 2015/095688 A1 | 6/2015 |
| WO | 2015/095694 A1 | 6/2015 |
| WO | 2015/150716 A2 | 10/2015 |
| WO | 2016/030631 A1 | 3/2016 |
| WO | 2017/094804 A1 | 6/2017 |
| WO | 2018/011275 A1 | 1/2018 |

OTHER PUBLICATIONS

Raghukumar, Thraustochytrid Marine Protists: Production of PUFAs and Other Emerging Technologies, Mar. Biotechnol. 10:631-640, Aug. 2008.
Yokoshi et al., Optimization of docosahexaenoic acid production by Schuzochytrium limacinum SR21, Appl. Microbiol. Biotechnol. 49:72-76, Jan. 1998.
Hadaruga et al., Thermal and oxidative stability of Atlantic salmon oil (*Salmo salr* L.) and complexation with B-cyclodextrin, Beilstein. J. Org. Chem. 12:179-191, Feb. 2016.
Lin et al., Optimization of Enzymatic Cell Disruption for Improving Lipid Extraction from *Schizochytrium* sp. through Response Surface Methodology, J. Oleo Sci. 67:215-224, Jan. 2018.
Yel et al., Comparison of Cell Disruption and Lipid Extraction Methods for Improving Lipied Content of *Schizochytrium* sp. S31, J. Mol. Biol. Biotechnol. 1: 9-12, Apr. 2017.
Veynachter et al., Centrifugation et decantation, Techniques de l'ingénieur F2730, Mar. 2007.
Pages et al., Raffinage des huiles et des corps gras et élimination des contaminants, OCL 17:86-99, Mar. 2010.
Jin et al., Enzyme-assited extraction of lipids directly from the culture of the oleaginous yeast Rhodosporidium Toruloides, Bioresource Technology 111:378-382, Feb. 2012.

(Continued)

*Primary Examiner* — Yate' K Cutliff
(74) *Attorney, Agent, or Firm* — BCF LLP

(57) ABSTRACT

The present invention relates to a method for extracting an oil rich in polyunsaturated fatty acids (PUFA), in particular an oil of microorganisms rich in docosahexaenoic acid (DHA, C22:6n3), in particular oils comprising more than 60% of PUFA relative to the total mass of fat.

18 Claims, No Drawings

(56) References Cited

OTHER PUBLICATIONS

Lin et al., "Optimization of enzymatic cell disruption for imporving lipid extraction from *Schyzochytrium* sp. through response surface methodology", Journal of Oleo Science 2018, 67, 215-224.

Fedorova-Dahms et al., "Safety evaluation of DHA-rich algal oil from *Schizochytrium* sp". Food and Chemical Toxicology, 2011, vol. 49, 3310-3318.

Folch et al., "A simple method for the isolation and purification of total lipides from animal tissues", J Biol Chem. 1957, vol. 226, No. 1, 497-509.

Hamilton et al. "Heterotrophic Production of Omega-3 Long-Chain Polyunsaturated Fatty Acids by Trophically Converted Marine Diatom Phaeodactylum tricornum", Marine Drugs, 2016, vol. 14, No. 53, 1-10.

Ghasemifard et al., "Omega-3 long chain fatty acid "bioavailability": a review of evidence and methodological considerations" Progress in Lipid Research, 2014, vol. 56, 92-108.

Tsuzuki, "Study of the Formation of trans Fatty Acids in Model Oils (triacylglycerols) and Edible Oils during the Heating Process" JARQ, 2012, vol. 46 No. 3, 215-220.

Miyazaki et al., "An Improved Enzymatic Indirect Method for Simultaneous Determinations of 3-MCPD Esters and Glycidyl Esters in Fish Oils", Journal of Oleo Science, 2017, 66, (10), pp. 1085-1093.

Jouhet et al. "Transient increase of phosphatidylcholine in plant cells in response to phosphate deprivation", FEBS Letters 544, 2003, 63-68.

Mansour et al. "Characterization of Oilseed Lipids from "DHA-Producing Camelina sativa": A New Transformed Land Plant Containing Long-Chain Omega-3 Oils", Nutrients, 2014, vol. 6, No. 2, 776-789.

Ruiz-Lopez et al., "Successful high-level accumulation of fish oil omega-3 long chain polyunsaturated fatty acids in a transgenic oilseed crop", The Plant Journal, 2014, vol. 77, No. 2, 198-208.

Rosenthal et al., "Aqueous and enzymatic processes for edible oil extraction" Enzyme and Microbial Technology 1996, vol. 19, 402-420.

\* cited by examiner

METHOD FOR EXTRACTING AN OIL RICH IN POLYUNSATURATED FATTY ACIDS (PUFA)

CROSS-REFERENCE TO RELATED APPLICATIONS

This application is a national phase filing under 35 U.S.C. 371 of International Application No. PCT/EP2019/074461, filed on Sep. 13, 2019, which claims the benefit of priority from French Patent Application No. FR 1858293, filed on Sep. 14, 2018, which is incorporated by reference herein in its entirety.

FIELD OF THE INVENTION

The present invention relates to a process for extracting an oil rich in polyunsaturated fatty acids (PUFAs), in particular an oil of microorganisms rich in docosahexaenoic acid (DHA, C22:6n3), in particular oils comprising more than 60% PUFA in relation to the total mass of fat.

BACKGROUND ART

There is today a demand for concentrated oils with high PUFA contents, namely for the supply of concentrated products such as concentrated oil capsules that make it possible to reduce the number of unit doses needed for an equivalent amount of PUFA. To obtain oils with a high PUFA content (for example above 55% DHA), the oils are concentrated by a process that converts triglycerides to ethyl esters involving the use of solvents such as ethanol. Ethyl esters are an artificial chemical form, they do not exist in nature. The bioavailability of fatty acids in the form of ethyl esters is much less than in the form of triglycerides (Ghasemifard et al., 2014). Moreover, the process removes the vitamins and antioxidants present in the crude oil. Consequently, the concentrated oil is more vulnerable to oxidation.

It is therefore advantageous to obtain an oil naturally rich in PUFAs, the composition of which is as close as possible to the liposoluble substances of the producing organism with a minimum of contaminants produced during treatments. However, the extraction of PUFA-rich oils runs into particular difficulties with this high PUFA content, which limits the amounts of fatty acids extracted from the biomass.

The extraction processes currently used involve the addition of sodium (WO 2011/153246), solvent (US 2014/350222) and/or high temperatures for several hours (WO 2015/095694) which can reduce the quality of the oil obtained and of the co-product (defatted biomass). Indeed, temperature is a factor that induces the formation of trans fatty acids from cis fatty acids. However, regulations impose a maximum content of less than 1% trans fatty acids in edible oils. The fatty acids of PUFA-producing microorganisms are naturally in cis conformation, any formation of trans fatty acids therefore reduces the quality of the oil. Temperature can also cause the formation of 2-MCPD, 3-MCPD and glycidol, toxic compounds whose content is regulated (glycidol) or in the process of being regulated (2- and 3-MCPD). It is important to seek to optimize the quality of the oil and to have as little as possible, in particular for the use of oils in baby food.

The addition of sodium during extraction, in the form of sodium sulfate or sodium chloride, is a known process (WO 2011/153246). Unfortunately, sodium is found in the defatted biomass. This reduces the advantage of this biomass, which is also rich in proteins, for animal feed in particular. In addition, the efficiency of a process with addition of sodium and temperatures less than or equal to 70° C. is limited in terms of extraction yield from a biomass with more than 60% PUFA.

The invention meets this demand with a novel process for extracting high-PUFA-content fats, which improves the extraction yields of these oils, and in particular the extraction of PUFA from the biomass in which they are contained, while preserving the quality of the oil.

DISCLOSURE OF THE INVENTION

The invention relates to a novel process for extracting a PUFA-rich oil from a biomass of an oil producing organism comprising said oil, the process comprising the steps (a) of cell lysis of the oil-producing organism biomass and (b) of mechanical separation of the oil from the lysed biomass and recovery of the crude oil, the process being characterized in that the cell lysis comprises two parts:

(a1) a first part carried out at a first temperature, then
(a2) a second part of continued lysis at a second temperature lower than the first.

The process according to the invention can be carried out for any type of organism producing an oil with a high PUFA content, whether it is an animal, in particular a marine animal, oilseed plants or microorganisms.

The process according to the invention is particularly suitable for extracting microbial oils with a high PUFA content. It does not involve the addition of solvents for oil extraction.

The invention also relates to a PUFA-rich oil obtained by the process, whether crude or refined or the diluted oil comprising the oil extracted with the process according to the invention which is mixed with another oil.

The invention also relates to a pharmaceutical, cosmetic or food composition that comprises an oil obtained by the process according to the invention, whether crude, refined or diluted.

The invention also relates to the use of an oil obtained by the process according to the invention, crude, refined or diluted, for food for human or animal consumption, in particular for feeding newborns, children, or pregnant or nursing women.

It also relates to a composition, in particular a nutraceutical composition or a food, which comprises oil obtained by the process according to the invention, whether crude, refined or diluted.

DETAILED DESCRIPTION OF THE INVENTION

PUFAs are well known to the person skilled in the art, in particular for their use as food additives or for the preparation of functional foods, in particular for infant milks or for pregnant or nursing women. Particular mention may be made of docosahexaenoic acid (DHA, C22:6n3), DPA (docosapentaenoic acid, C22:5n6), arachidonic acid (ARA, C20:4n6) or eicosapentaenoic acid (EPA, C20:5n3). Depending on the producing organisms considered, the oils comprise mostly DHA, EPA or ARA, or mixtures of several PUFAs.

ARA-producing organisms are well known. Particular mention may be made of filamentous fungi of the genus *Mortierella alpina*. EPA-producing organisms are also well known. Particular mention may be made of *Nannochloropsis gaditana*. DHA-producing organisms are also well known.

Particular mention may be made of the protists of the genera *Aurantiochytrium* or *Schizochytrium*. Plants are also good PUFA producers, in particular at seed level: linseed (*Linum usitatissimum* L.) oil can contain more than 50% alpha-linolenic acid (ALA); rapeseed (*Brassica napus*) is also a well-known ALA producer. Plants do not produce very long chain fatty acids (above C18). However, recently, transgenic *Camelina sativa* plants have been modified to produce DHA (Mansour et al., 2014) or EPA (Ruiz-Lopez et al. 2014). Seeds of oilseed plants typically contain between 20% (soybean) and 70% (dehydrated coconut) fat (Rosenthal et al., 1996).

The process according to the invention is particularly suitable for extracting PUFA-rich oils from oil-producing microorganisms. These microorganisms are particularly selected from filamentous fungi and protists.

The strains of microorganisms which make it possible to obtain such oils are industrial strains, i.e., according to the invention, strains the fat content of which represents at least 45% of the dry matter, preferentially at least about 50% of the dry matter, and which have a growth capacity at a cell density of at least 50 g/L, preferentially at least 70 g/L, more preferentially at least 100 g/L.

The skilled person is familiar with industrial strains of PUFA-producing microorganisms mainly among thraustochytrids, Dinophyceae, diatoms, Eustigmatophyceae, in particular microorganisms of the genera *Cryptecodinium, Schizochytrium, Thraustochytrium* or *Aurantiochytrium* for DHA production.

Particular mention may be made of *Cryptecodinium cohnii* M64245, *Crypthecodinium cohnii* FJ821501, *Crypthecodinium cohnii* CCAP 1104/3 (WO2016030631), *Crypthecodinium cohnii* CCAP 1104/5 or *Cryptecodinium cohnii* CCAP 1104/4, *Aurantiochytrium limacinum* AB022107; *Aurantiochytrium limacinum* HM042909; *Aurantiochytrium limacinum* JN986842; *Aurantiochytrium limacinum* SL1101 JN986842; *Aurantiochytrium mangrovei; Aurantiochytrium mangrovei* DQ323157; *Aurantiochytrium mangrovei* DQ356659; *Aurantiochytrium mangrovei* DQ367049; *Aurantiochytrium mangrovei* CCAP 4062/2; *Aurantiochytrium mangrovei* CCAP 4062/3; *Aurantiochytrium mangrovei* CCAP 4062/4; *Aurantiochytrium mangrovei* CCAP 4062/5; *Aurantiochytrium mangrovei* CCAP 4062/6; *Aurantiochytrium mangrovei* CCAP 4062/1; *Aurantiochytrium* sp. AB052555; *Aurantiochytrium* sp. AB073308; *Aurantiochytrium* sp. ATCC PRA276 DQ836628; *Aurantiochytrium* sp. BL10 FJ821477; *Aurantiochytrium* sp. LY 2012 PKU Mn5 JX847361; *Aurantiochytrium* sp. LY2012 JX847370; *Aurantiochytrium* sp. N1-27; *Aurantiochytrium* sp. SD116; *Aurantiochytrium* sp. SEK209 AB290574; *Aurantiochytrium* sp. SEK217 AB290572; *Aurantiochytrium* sp. SEK 218 AB290573; *Aurantiochytrium* sp. 18W-13a; *Botryochytrium radiatum; Botryochytrium radiatum* Raghukumar 16; *Botryochytrium radiatum* SEK353; *Botryochytrium* sp.; *Botryochytrium* sp. BUTRBC 143; *Botryochytrium* sp. Raghukumar 29; *Oblongichytrium minutum; Oblongichytrium multirudimentalis; Oblongichytrium* sp. SEK347; *Parieticytrium sarkarianum; Parieticytrium sarkarianum* SEK351; *Parieticytrium sarkarianum* SEK364; *Parieticytrium* sp. F3-1; *Parieticytrium* sp. H1-14; *Parieticytrium* sp. NBRC102984; *Phytophthora infestans; Schizochytrium aggregatum* DQ323159; *Schizochytrium aggregatum* DQ356661; *Schizochytrium aggregatum; Schizochytrium limacinum; Schizochytrium limacinum* OUC166 HM042907; *Schizochytrium mangrovei; Schizochytrium mangrovei* FB1; *Schizochytrium mangrovei* FB3; *Schizochytrium mangrovei* FB5; *Schizochytrium minutum;* *Schizochytrium* sp. ATCC20888 DQ367050; *Schizochytrium* sp. KGS2 KC297137; *Schizochytrium* sp. SKA10 JQ248009; *Schizochytrium* sp. ATCC 20111; *Schizochytrium* sp. ATCC 20888 (WO1991007498); *Schizochytrium* sp. ATCC 20889; *Schizochytrium* sp. ATCC 26185; *Schizochytrium* sp. BR2.1.2; *Schizochytrium* sp. BUCAAA 032; *Schizochytrium* sp. BUCAAA 093; *Schizochytrium* sp. BUCACD 152; *Schizochytrium* sp. BUCARA 021; *Schizochytrium* sp. BUCHAO 113; *Schizochytrium* sp. BURABQ 13; *Schizochytrium* sp. BURARM 802; *Schizochytrium* sp. CCAP 4087/3 (WO2017012931); *Schizochytrium* sp. CCAP 4087/1; *Schizochytrium* sp. CCAP 4087/4; *Schizochytrium* sp. CCAP 4087/5; *Schizochytrium* sp. FJU-512; *Schizochytrium* sp. KH105; *Schizochytrium* sp. KK17-3; *Schizochytrium* sp. KR-5; *Schizochytrium* sp. PJ10.4; *Schizochytrium* sp. SEK 210; *Schizochytrium* sp. SEK 345; *Schizochytrium* sp. SEK 346; *Schizochytrium* sp. SR21; *Schizochytrium* sp. TIO01; *Sicyoidochytrium minutum* SEK354; *Sicyoidochytrium minutum* NBRC 102975, *Sicyoidochytrium minutum* NBRC 102979; *Thraustochytriidae* sp. BURABG162 DQ100295; *Thraustochytriidae* sp. CG9; *Thraustochytriidae* sp. LY2012 JX847378; *Thraustochytriidae* sp. MBIC11093 AB183664; *Thraustochytriidae* sp. NIOS1 AY705769; *Thraustochytriidae* sp. #32 DQ323161; *Thraustochytriidae* sp. #32 DQ356663; *Thraustochytriidae* sp. RT49 DQ323167; *Thraustochytriidae* sp. RT49 DQ356669; *Thraustochytriidae* sp. RT49; *Thraustochytriidae* sp. The12 DQ323162; *Thraustochytriidae* sp. The12; *Thraustochytrium aggregatum; Thraustochytrium aggregatum* DQ356662; *Thraustochytrium aureum; Thraustochytrium aureum* DQ356666; *Thraustochytrium gaertnerium; Thraustochytrium kinnei; Thraustochytrium kinnei* DQ323165; *Thraustochytrium motivum; Thraustochytrium multirudimentale; Thraustochytrium pachydermum; Thraustochytrium roseum; Thraustochytrium* sp. 13A4.1; *Thraustochytrium* sp. ATCC 26185; *Thraustochytrium* sp. BL13; *Thraustochytrium* sp. BL14; *Thraustochytrium* sp. BL2; *Thraustochytrium* sp. BL3; *Thraustochytrium* sp. BL4; *Thraustochytrium* sp. BL5; *Thraustochytrium* sp. BL6; *Thraustochytrium* sp. BL7; *Thraustochytrium* sp. BL8; *Thraustochytrium* sp. BL9; *Thraustochytrium* sp. BP3.2.2; *Thraustochytrium* sp. BP3.3.3; *Thraustochytrium* sp. caudivorum; *Thraustochytrium* sp. CHN-1; *Thraustochytrium* sp. FJN-10; *Thraustochytrium* sp. HK1; *Thraustochytrium* sp. HK10; *Thraustochytrium* sp. HK5; *Thraustochytrium* sp. HK8; *Thraustochytrium* sp. HK8a; *Thraustochytrium* sp. KK17-3; *Thraustochytrium* sp. KL1; *Thraustochytrium* sp. KL2; *Thraustochytrium* sp. KL2a; *Thraustochytrium* sp. ONC-T18; *Thraustochytrium* sp. PJA10.2; *Thraustochytrium* sp. T R1.4; *Thraustochytrium* sp. TRR2; *Thraustochytrium striatum; Thraustochytrium striatum* ATCC24473 (WO2017131188); *Thraustochytrium striatum* DQ323163; *Thraustochytrium striatum* DQ356665; *Thraustochytrium visurgense; Ulkenia amoeboidea* SEK 214; *Ulkenia profunda; Ulkenia profunda* BUTRBG 111; *Ulkenia* sp.; *Ulkenia* sp. ATCC 28207 (WO1998003671); *Ulkenia visurgensis; Ulkenia visurgensis* BURAAA 141; *Ulkenia visurgensis* ATCC 28208; Thraustochytrids deposited at the ATCC under accession numbers PTA-9695, PTA-9696, PTA-9697 and PTA-9698 (US 2010-239533).

For the production of EPA-rich oils, mention may be made of *Phaeodactylum tricornutum* (Pt1) Bohlin Strain 8.6 CCMP2561 (WO2015008160); *Nitzschia brevirostris* (CCAP 1052/21; WO2013136025); *Nitzschia laevis* (UTEX 2047; WO2008004900); *Pythium irregulare* (U.S. Pat. No. 9,074,160); *Nannochloropsis limnetica* (WO2016059262);

*Nannochloropsis salina; Nannochloropsis avicula; Nannochloropsis acceptata; Nannochloropsis oculata* CCAP849/1; *Nannochloropsis pseudotenelloides; Nannochloropsis gaditana; Nannochloropsis* sp. CCAP211/46; *Nannochloropsis saprophila; Chlorella protothecoides* CCAP211/17 (WO201115041); *Chlorella ellipsoidea; Chlorella minutissima; Chlorella zofinienesi; Chlorella luteoviridis* CCAP211/3; *Chlorella kessleri; Chlorella sorokiniana* CCAP211/8K; *Chlorella fiusca* var. *vacuolata; Chlorella* sp.; *Chlorella emersonii; Monodus subterraneus.*

For the production of ARA-rich oils, mention may be made of *Mortierella elongata* IF08570, *Mortierella exigua* IF08571, *Mortierella hygrophila* IF05941, *Mortierella alpina* IF08568, ATCC16266, ATCC32221, ATCC42430, CBS219.35, CBS224.37, CBS250.53, CBS343.66, CBS527.72, CBS529.72, CBS608.70, and CBS754.68 (WO 2015/095696).

The process according to the invention is particularly suitable for extracting PUFAs from organisms that comprise PUFA-rich oils, in particular at contents comprising more than 50% PUFA in relation to the total mass of fat. It finds its best applications to extract PUFAs from microorganisms that produce oils containing more than 60% PUFA in relation to the total mass of fat, advantageously at least 62% PUFA, more advantageously at least 65% PUFA, preferably more than 67%, more preferentially at least 70%, even more preferentially 75% PUFA in relation to the total mass of fat.

However, the benefits observed significantly on high PUFA contents are also found for extracting PUFAs from microorganisms that produce less rich oils, but with amounts of PUFA that remain significant, from 40% to 50% PUFA in relation to the total mass of fat.

According to a preferred embodiment of the invention, the PUFA to be extracted is DHA, or a DHA+DPA mixture, the microorganisms used being microorganisms producing oils rich in DHA or in DHA+DPA.

Particular mention may be made of *Aurantiochytrium mangrovei* CCAP 4062/2; *Aurantiochytrium mangrovei* CCAP 4062/3; *Aurantiochytrium mangrovei* CCAP 4062/4; *Aurantiochytrium mangrovei* CCAP 4062/5; *Aurantiochytrium mangrovei* CCAP 4062/6; *Aurantiochytrium mangrovei* CCAP 4062/1; *Schizochytrium* sp. CCAP 4087/3; *Schizochytrium* sp. CCAP 4087/1; *Schizochytrium* sp. CCAP 4087/4; *Schizochytrium* sp. CCAP 4087/5; or the Thraustochytrids deposited with the ATCC under accession numbers PTA-9695, PTA-9696, PTA-9697 and PTA-9698. The process according to the invention may be carried out with microorganisms that produce oils particularly rich in DHA, in particular the strains *Aurantiochytrium mangrovei* CCAP4062/7 and CCAP4062/8 and *Schizochytrium* sp. CCAP4087/7.

The biomass of producing organisms can undergo a first treatment to allow this cell lysis. For example, for oilseed plant seeds, the biomass may undergo a series of treatments known to separate the grains from the husks, followed by a first grinding and suspension of the ground material before lysis is carried out.

For a biomass of microorganisms derived from a culture of microorganisms, the biomass can be derived directly from the fermentation must. It can be washed to remove certain solubles (in particular by filtration to remove the fermentation medium and washing with water) and resuspended for the lysis step (a). The microorganism biomass can also be a dried or freeze-dried biomass that has been stored and resuspended prior to the lysis step. These pretreatments of the microbial biomass to facilitate the implementation of the lysis step (a) are well known to the skilled person.

The cell lysis step (a) is advantageously carried out on a biomass suspension. This suspension preferably has a dry matter content of 5 to 20% by mass, generally from 8 to 10% by mass.

Cell lysis is done by enzymatic or mechanical lysis. The temperature of the first part of lysis is preferably at least 50° C. while remaining below temperatures that would degrade the composition of oils in addition to promoting cell lysis, i.e., temperatures below 95° C., or even below 90° C., preferably below 80° C., even more preferentially below 70° C.

The enzymes that can be used are known, particularly those described in WO2015/095688, WO2011/153246, U.S. Pat. No. 6,750,048 and WO2015/095694, in particular proteases or cellulases such as the enzymes marketed by Novozyme under the names Alcalase 2.5 L, Alcalase 2.4 L, Alcalase 3.0 T, Novozym 37071, Flavourzyme 1000 L, Novozym FM 2.4 L, Protamex, Viscozyme. The conditions of use are those recommended by the supplier, the temperature being that recommended for optimal enzyme activity, at least 50° C. and up to 70° C., preferably about 65° C. Advantageously, enzymatic lysis is carried out in an oxygen-poor atmosphere. Generally, the oxygen concentration is less than 1% by mass.

Mechanical lysis methods are also well known, in particular by ball mills, mixer-dispersers, high-pressure homogenizers, pin mills or impact mills, ultrasonic, pulsed electric fields. As devices for carrying out these mechanical lysis methods, particular mention may be made of (manufacturer's name in brackets) for the ball mill: Discus-1000 (Netzsch); ECM-AP60 (WAB); for the high-pressure homogenizer: Ariete (GEA); for the mixer-disperser: 700-X (Silverson); for the pin mill: Contraplex (Hosakawa); for the impact mill: Condux (Netzsch).

The first part (a1) of the lysis is carried out under the usual conditions recommended by the state of the art for cell lysis, in particular in terms of the duration of the enzymatic lysis or the grinding cycles.

The step (a2) of continuation of the lysis completes the lysis by modifying the conditions of implementation without having to extract the lysed biomass beforehand. The modification of the implementation conditions is a modification of temperature, but does not include substantial modifications of the suspension medium comprising the partially lysed biomass, such as the addition of salt, acid or base. A substantial modification of the suspension medium prior to or concomitant with the drop in temperature is not a priori a "continuation of the lysis" according to the invention. Such substantial modifications of the suspending medium after lysis are described in US 2011/295028 and US 2015/176042 which do not allow an efficient extraction of high-PUFA-content oils.

Advantageously, enzymatic lysis consists essentially of these two parts (a1) and (a2) which are essentially distinguished by a drop in temperature when moving to the second part (a2) of the lysis.

The lysis temperature in this second part is at least 10° C. lower than in the first part. Preferably, the temperature of the second part of lysis is less than or equal to 40° C., advantageously going from 5° C. to 40° C., more advantageously going from 10° C. to 35° C., or even from 15° C. to 30° C., preferably from 20° C. to 30° C. This second part (a2) of lysis at lower temperature, or end of lysis, is advantageously carried out for at least 30', which can go up to 30 h. The state of the art teaches us to maintain the temperature above 40° C., or even to increase the temperature above 80° C. to improve the extraction during or after the lysis step, this whether the starting biomass is microorganisms (WO2018011275) or oilseeds (Rosenthal et al., 1996). Surprisingly, the inventors found that the reverse (lower temperature) gives a better result, especially for high-PUFA-content oils. The temperature of step (a2) is not increased at the end of lysis before the separation step (b).

The mechanical separation (b) of an oil from a lysed biomass is also well known to the skilled person, as a gravity separation, in particular by centrifugation as described in patent application WO 01/53512. Continuous separation can also be used, in particular by centrifugal plate separator. Such separators are known to continuously extract oils from complex media comprising solid residues and water, as described in patent application WO 2010/096002, in particular marketed by the companies Alfa Laval, Flottweg or GEA Westfalia, among others. This continuous separation step is preferred in the process used to obtain the oil according to the invention.

Depending on the PUFA content of the producing organism, the crude oils obtained by the process according to the invention may have very high contents of PUFA, in particular of DHA, of more than 60% PUFA in relation to the total mass of fat, advantageously at least 62% PUFA, more advantageously at least 65% PUFA, preferably more than 67%, more preferentially at least 70%, even more preferentially 75% PUFA in relation to the total mass of fat extracted.

The oils obtained by the process according to the invention are essentially in the form of triglycerides. Triglycerides advantageously represent at least 80% of the total mass of fat, more advantageously at least 90%, even more advantageously at least 93% of the total mass of fat. The triglyceride content is for example analyzed by thin-layer chromatography (Jouet et al., 2003).

Generally, the extraction of oil from biomass with the process according to the invention provides a slight increase in the content of PUFA, in particular of DHA and of DPA, promoting the extraction of these PUFA over lower molecular weight saturated fatty acids. However, this concentration does not substantially modify the intrinsic properties of the oil contained in the biomass, in particular the triglyceride content. In any case, the oil according to the invention is an oil that has not undergone substantial modifications of its fatty acid content by the addition of PUFA, for example in the form of esters, by concentration and/or by the removal of saturated fatty acids such as palmitic acid.

The oil obtained is generally an oil called crude oil, which can be used as is or can be refined, in particular to facilitate its storage, by preventing it from becoming rancid, or to change its color to make it more acceptable to a consumer. These refining steps are well known to the skilled person, in particular degumming, neutralization of free fatty acids, decolorization and deodorization. They remove (completely or partly) phospholipids, pigments, volatiles and free fatty acids. In fact, these methods do not substantially modify the relative content of saturated or unsaturated fatty acids or of triglycerides in the refined oil obtained in relation to crude oil.

The invention therefore also relates to a process for extracting an oil rich in PUFA as defined above, which also comprises a refining step (c).

Some processes of the state of the art have a so-called "winterization" step carried out on crude or refined oils, in particular to remove saturated fatty acids, with the effect of increasing the PUFA content (WO 02/10322). Oils extracted according to the invention, whether crude or refined, do not a priori require "winterization" to be exploited. However, the skilled person may choose to add such a "winterization" step if he finds any commercial advantage for his final product.

Depending on the PUFA-rich oil-producing microorganisms employed, in particular DHA-producing microorganisms, the oil obtained by the process according to the invention may contain more than 10 mg of native carotenoids per kg of oil, or even more than 30 mg/kg, preferentially more than 40 mg/kg, even more preferentially more than 60 mg/kg, or at least 65 mg/kg. The carotenoids present are mainly astaxanthin and beta-carotenes. The oil contains more than 20 mg/kg of astaxanthin, or even more than 30 mg/kg, more preferentially more than 40 mg/kg. Cantaxanthin is also present but in lesser amounts. Other carotenoids such as lutein and zeaxanthin may be present but they are at the limit of detection of the method used. The term "native carotenoids" means that the carotenoids have not been added, they come from the same biomass as the oil and are extracted from this biomass along with the oil. They are produced by the strain under heterotrophic fermentation conditions, without any particular stimulus. These native carotenoids are therefore present throughout the process, protecting the fatty acids, in particular DHA, against oxidation. The refining process can remove pigments, so the refined oil may contain fewer carotenoids, if any.

Crude or refined oils can also be diluted for further use.

The invention therefore also relates to a process for extracting a PUFA-rich oil as previously defined, which further comprises a step (d) of diluting the crude oil obtained in the mechanical separation step (b) or the refined oil obtained in the refining step (c).

The oils used to dilute the PUFA-rich oil obtained by the process according to the invention are generally and preferably vegetable oils suitable for human or animal consumption. Particular mention may be made of sunflower, rapeseed, soybean, walnut, sesame, hemp, hazelnut, argan, olive, linseed or any other oil suitable for food use. The added oil may also be an oil containing other PUFAs, in particular DHA, ARA and/or EPA, in particular other oils of microbial origin or fish oils.

The invention also relates to a composition comprising a PUFA-rich oil obtained by the process according to the invention, whether crude, refined or diluted.

A composition according to the invention may comprise one or more excipients. An excipient is a component, or mixture of components, which is used in the present invention to give desirable characteristics to the composition for its storage and use, including foods and pharmaceutical, cosmetic and industrial compositions. An excipient may be described as a "pharmaceutically acceptable" excipient when it is added to a pharmaceutical composition whose properties are known from the pharmacopoeia to be used in contact with human and animal tissues without excessive toxicity, irritation, allergic reaction or other complications. Various excipients may be used such as an organic or mineral base, an organic or mineral acid, a pH buffer, a stabilizer, an antioxidant, an adhesion agent, a release agent, a coating agent, an outer phase component, a controlled release component, a surfactant, a humectant, a filler, an emollient, or combinations thereof.

Depending on their destination, the compositions according to the invention are in particular pharmaceutical, cosmetic, nutraceutical compositions or foods.

Foods are intended for both humans and animals and include solid, pasty or liquid compositions. Particular mention may be made of common foods, liquid products, including milks, drinks, therapeutic and nutritional beverages, functional foods, supplements, nutraceuticals, infant formula, including formula for premature infants, foods for pregnant or nursing women, foods for adults, geriatric foods and animal feeds.

The PUFA-rich oil obtained by the process according to the invention, whether crude or refined, or the biomass containing it can be used directly as or added as an additive in an oil, a spread, another fat ingredient, a beverage, a soybean-based sauce, dairy products (milk, yogurt, cheese, ice cream), bakery products, nutritional products, for example in the form of nutritional supplements (in capsule or tablet form), vitamin supplements, food supplements, dilution powders for beverages, such as energy drinks or milk powders for infant formulations, finished or semi-finished powdered food products, etc., according to the known uses of the person skilled in the art.

Pet food is also known to the skilled person. They are in particular intended for livestock, such as cows, pigs, chickens, sheep, goats or in fish farming for shellfish or farmed fish.

Pharmaceutical compositions comprising a PUFA-rich oil are also known to the skilled person, the oil being used alone or in combination with other medicinal products.

The PUFA-rich oil obtained by the process according to the invention, crude or refined, or the biomass containing it, can be formulated in the form of single-dose compositions, in particular in the form of tablets, capsules, powders, granules, suitable for oral administration.

The invention also relates to the use of a PUFA-rich oil obtained by the process according to the invention, crude, refined or diluted, for food for human or animal consumption, in particular for feeding newborns, children, or pregnant or nursing women.

Such uses are well known to the skilled person, in particular described in patent application WO 2010/107415 and on the website of the firm DSM (https://www.dsm.com/markets/foodandbeverages/en_US/products/nutritional-lipids/life-dha.html).

EXAMPLES

Example 1: Fermenter Cultures of High-DHA-Content Strains

The cultures are carried out in fermenters (bioreactors) with a 1 to 5 L useful volume with dedicated automated handling and supervision by computer station. They are carried out using two strains of *Aurantiochytrium mangrovei* and with two different culture protocols. The system is regulated at pH 5 via the addition of base (NH40H for example b1 and b2 and with NaOH for example a) with pH adjustment carried out over the entire duration of the culture, and providing a nitrogen supply (in the case of examples b1 and b2). The culture temperature was set at 30° C. then 22° C. and finally 18° C. at the end of the culture.

Strain CCAP4062/7 is used for example a and b1 while strain FCCB1897 is used for example b2.

The composition of the culture media is given in Table 1.

TABLE 1

|  | a | b1 and b2 |  |
|---|---|---|---|
| CaCl2, 2H2O | 0.55 | 0.55 | g/L |
| MgSO4, 7H2O | 4-8 | 4-8 | g/L |
| H3BO3 | 0.00875-0.175 | 0.00875-0.0175 | g/L |
| K2SO4 | 2.08 | 0.00 | g/L |

TABLE 1-continued

|  | a | b1 and b2 |  |
|---|---|---|---|
| KH2PO4 | 4.00 | 4.00 | g/L |
| Na4EDTA, 2H2O | 0.12 | 0.12 | g/L |
| FeSO4, 7H2O | 0.04 | 0.04 | g/L |
| (NH4)2SO4 | 9.00 | 1.00-2.00 | g/L |
| MnCl2, 4H2O | 0.0108 | 0.0108 | g/L |
| ZnSO4, 7H2O | 0.0108 | 0.0108 | g/L |
| CoCl2, 6H2O | 0.000108 | 0.000108 | g/L |
| Na2MoO4, 2H2O | 0.000108 | 0.000108 | g/L |
| Na2SeO3 | 1.73E−07 | 1.73E−07 | g/L |
| CuSO4, 5H2O | 0.0072 | 0.0072 | g/L |
| NiSO4, 6H2O | 0-0.0056 | 0-0.0056 | g/L |
| Thiamine | 0.0320 | 0.0320 | g/L |
| Vitamin B12 | 0.0005 | 0.0005 | g/L |
| Pantothenate | 0.0108 | 0.0108 | g/L |
| Antifoam Biospumex 153K | 0.40 | 0.40 | mL/L |
| Glucose, 1 H2O | 55.00 | 55.00 | g/L |

Glucose additions in the form of an enrichment solution are made with a carbon:nitrogen:phosphorus (CNP) molar ratio of 533:11:1 (example a) or with a solution composed only of glucose (examples b1 and b2).

Culture Monitoring:

The total biomass concentration is monitored by measuring the dry mass (filtration on GF/F filter, Whatman, then oven drying, at 105° C., for a minimum of 24 h before weighing). Fatty acid analyses are carried out according to a method adapted from standard ISO 12966-2 for biomass, and according to the European Pharmacopoeia 9.0 (2.4.29.) for oils.

The fatty acid profiles of the biomasses obtained under conditions a, b1 and b2 are given in Table 2, as a percentage in relation to total fatty acids. SFA: saturated fatty acids.

TABLE 2

|  | a | b1 | b2 |
|---|---|---|---|
| C10:0 | 0.0 | 0.0 | 0.0 |
| C11:0 | 0.0 | 0.0 | 0.0 |
| C12:0 | 0.0 | 0.0 | 0.0 |
| C13:0 | 0.0 | 0.0 | 0.0 |
| C14:0 | 0.8 | 1.2 | 0.3 |
| C14:1 | 0.0 | 0.0 | 0.0 |
| C15:0 | 0.0 | 0.1 | 1.7 |
| C15:1 | 0.0 | 0.0 | 0.0 |
| C16:0 | 13.6 | 19.6 | 10.9 |
| C16:1 | 0.1 | 0.2 | 0.2 |
| C16:2 | 0.0 | 0.0 | 0.0 |
| C16:3 | 0.0 | 0.0 | 0.0 |
| C16:4 | 0.0 | 0.0 | 0.0 |
| C17:0 | 0.0 | 0.0 | 0.0 |
| C17:1 | 0.0 | 0.0 | 0.3 |
| C18:0 | 0.5 | 0.6 | 0.6 |
| C18:1 | 0.2 | 0.3 | 0.4 |
| C18:2 | 0.0 | 0.0 | 0.0 |
| C18:3n3 | 0.2 | 0.1 | 0.2 |
| C18:3n6 | 0.1 | 0.1 | 0.1 |
| C18:4n3 | 0.3 | 0.3 | 0.3 |
| C20:0 | 0.1 | 0.1 | 0.1 |
| C20:4n6 (ARA) | 0.1 | 0.0 | 0.1 |
| C20:5n3 (EPA) | 0.4 | 0.6 | 0.6 |
| C21:0 | 0.0 | 0.1 | 0.0 |
| C22:0 | 0.1 | 0.0 | 0.0 |
| C22:5n3 (DPAn3) | 0.2 | 0.0 | 0.2 |
| C22:5n6 (DPAn6) | 12.9 | 9.6 | 12.7 |
| C22:6n3 (DHA) | 66.6 | 62.5 | 70.1 |
| DHA + DPA | 79.7 | 72 | 83 |
| SFA | 15.1 | 22 | 11.4 |
| DHA/DPA | 5.2 | 6.5 | 5.5 |
| DHA/AGS | 4.4 | 2.9 | 6.2 |
| (DHA + DPA)/SFA | 5.3 | 3.3 | 7.3 |

Example 2: Culture Under Industrial Conditions of High-DHA-Content Strains

High-DHA-content *Aurantiochytrium mangrovei* strains produce a biomass with a similar fatty acid composition when grown in industrial size fermenters, such as 10 m3 (example d) or 180 m3 (example e) tanks, under similar conditions, with culture medium b and glucose additions in the form of an enrichment solution are made with a carbon:nitrogen:phosphorus (CNP) molar ratio of 533:0.4:1.

The fatty acid profiles of the biomass for examples d and e are given in Table 3, as a percentage in relation to total fatty acids.

TABLE 3

|  | 10m3 | 180m3 |
|---|---|---|
| C10:0 | 0.0 | 0.0 |
| C11:0 | 0.0 | 0.0 |
| C12:0 | 0.0 | 0.0 |
| C13:0 | 0.0 | 0.0 |
| C14:0 | 0.7 | 0.5 |
| C14:1 | 0.0 | 0.0 |
| C15:0 | 0.0 | 0.1 |
| C15:1 | 0.0 | 0.0 |
| C16:0 | 18.5 | 13.9 |
| C16:1 | 0.1 | 0.1 |
| C16:2 | 0.0 | 0.0 |
| C16:3 | 0.0 | 0.0 |
| C16:4 | 0.0 | 0.0 |
| C17:0 | 0.0 | 0.0 |
| C17:1 | 0.0 | 0.3 |
| C18:0 | 0.8 | 0.6 |
| C18:1n9 (c + t) | 0.0 | 0.0 |
| C18:2n6 (c + t) | 0.0 | 0.0 |
| C18:3n3 | 0.3 | 0.2 |
| C18:3n6 | 0.1 | 0.1 |
| C18:4n3 | 0.4 | 0.3 |
| C20:0 | 0.1 | 0.1 |
| C20:4n6 (ARA) | 0.2 | 0.1 |
| C20:5n3 (EPA) | 0.9 | 0.5 |
| C21:0 | 0.0 | 0.0 |
| C22:0 | 0.0 | 0.0 |
| C22:5n3 (DPAn3) | 0.2 | 0.2 |
| C22:5n6 (DPAn6) | 11.5 | 13.7 |
| C22:6n3 (DHA) | 65.5 | 68.3 |
| Fatty acids (% DM) | 44.0 | 60.0 |
| DHA + DPA | 77.0 | 82.2 |
| SFA | 20.1 | 15.2 |
| DHA/DPA | 5.6 | 4.9 |
| DHA/AGS | 3.3 | 4.5 |
| (DHA + DPA)/SFA | 3.8 | 5.4 |

Example 3: Extraction of Oil from the Biomass of High-DHA-Content Strains: Comparison of Yield with Different Processes The oil is extracted from the same biomass, produced under the conditions of example 2 and containing more than 60% DHA (Table 4).

TABLE 4

| Fatty acid composition of the biomass | |
|---|---|
| C14:0 | 0.9 |
| C16:0 | 18.1 |
| C18:0 | 0.6 |
| C18:1n-9 (c + t) | 0.0 |
| C18:2n-6 (c + t) | 0.0 |
| C18:3n-3 | 0.1 |
| C20:4n-6 | 0.1 |
| C20:5n-6 (EPA) | 0.7 |
| C22:5n-6 (DPA) | 9.8 |
| C22:6n-3 (DHA) | 63.9 |
| Fatty acids (% DM) | 50.7 |
| DHA + DPA | 73.7 |
| SFA | 20.6 |
| DHA/DPA | 6.52 |
| DHA/SFA | 3.1 |
| (DHA + DPA)/SFA | 3.6 |

Extraction is carried out according to various processes known to the skilled person, involving in particular chemical lysis (WO2015/095688A) or enzymatic lysis and addition of sodium sulfate (WO2011/153246) or changes in pH (WO2015/095694). Fat extraction yields in relation to the amounts present in the biomass are indicated in Table 5. Tests 1, 2 and 3 are carried out according to the teaching of the state of the art. Test 4 is carried out according to the invention.

TABLE 5

Oil extraction yield relative to the fat present in the biomass, according to the conditions of the different extraction tests.

| conditions | Trial 1 | Trial 2 | Trial 3 | Trial 4 |
|---|---|---|---|---|
| Enzyme lysis | Yes: Alcalase (1.2% DM) 2 H at 60° C. pH 7.3 | Yes: Alcalase (1.2% DM) 2 H at 60° C. pH 7.3 | no | Yes: Alcalase (1.2% DM) 7 H at 65° C. pH 8 |
| Acid hydrolysis | no | no | Yes: $H_2SO_4$ (2.5% FM) 5 H 40 at 70° C. pH 0.5 | no |
| Addition of acid or soda | NaOH 5 H at 70° C. pH 12, then $H_2SO_4$ 15 H at 70° C. pH 10.5 | $Na_2SO_4$ (10% FM) 25 H at 21° C. pH 7.3 | NaOH 10%, 16 H at 70° C. pH 7.7 | No, 17 H at 30° C. pH 8 |
| Change before centrifugation separation | $H_2SO_4$, pH 7 | 50° C. 1 H before centrifugation | no | no |
|  | centrifugation | centrifugation | centrifugation | centrifugation |
| Yield % fat | 22% | <1% | <1% | 53% |

DM: dry matter, FM: fresh matter.

Example 4: Extraction of Oil from the Biomass of High-DHA-Content Strains

The extraction of oil from the biomass produced in example 2 is carried out following the sequence:
(a) cell lysis by enzymatic means (e.g., with Alcalase 2.5 L or Alcalase 2.4 L or Novozym 37071 from Novozymes) for 4 h at a temperature of 65° C.,
(b) continuation of the lysis by lowering the temperature between 5 and 40° C., for a duration between 30 minutes and 30 h,
(c) mechanical separation of the oil by centrifugal plate separator.

The extraction yield is 60% lipids extracted from the biomass.

TABLE 6

Lipid profile of the extracted oil

|  | 10 m3 | 180 m3 |
|---|---|---|
| C10:0 | 0.0 | 0.0 |
| C11:0 | 0.0 | 0.0 |
| C12:0 | 0.0 | 0.0 |
| C13:0 | 0.0 | 0.0 |
| C14:0 | 0.3 | 0.0 |
| C14:1 | 0.0 | 0.0 |
| C15:0 | 0.0 | 0.0 |
| C15:1 | 0.0 | 0.0 |
| C16:0 | 15.4 | 8.3 |
| C16:1 | 0.0 | 0.0 |
| C16:2 | 0.0 | 0.0 |
| C16:3 | 0.0 | 0.0 |
| C16:4 | 0.0 | 0.0 |
| C17:0 | 0.0 | 0.0 |
| C17:1 | 0.0 | 0.0 |
| C18:0 | 0.4 | 0.4 |
| C18:1n9 (c + t) | 0.0 | 0.0 |
| C18:2n6 (c + t) | 0.0 | 0.0 |
| C18:3n3 | 0.0 | 0.0 |
| C18:3n6 | 0.0 | 0.0 |
| C18:4n3 | 0.2 | 0.0 |
| C20:0 | 0.0 | 0.0 |
| C20:4n6 (ARA) | 0.0 | 0.0 |
| C20:5n3 (EPA) | 0.5 | 0.2 |
| C21:0 | 0.0 | 0.0 |
| C22:0 | 0.0 | 0.0 |
| C22:5n3 (DPAn3) | 0.0 | 0.0 |
| C22:5n6 (DPAn6) | 11.6 | 15.4 |
| C22:6n3 (DHA) | 71.5 | 75.5 |
| DHA + DPA | 83.1 | 90.9 |
| SFA | 16.1 | 8.7 |
| DHA/DPA | 6.2 | 4.9 |
| DHA/SFA | 4.4 | 8.7 |
| (DHA + DPA)/SFA | 5.2 | 10.4 |

REFERENCES

EP0223960; EP1001034

WO 1994/008467; WO 1997/037032; WO 2001/054510; WO 02/10322; WO 03/049832; WO 2010/107415; WO2011/153246; WO 2012/035262; WO 2013/136025; WO 2013/136028; WO 2014/146098; WO 2015/004402; WO 2015/004403; WO2015/095688; WO2015/095694; WO 2015/150716; WO 2016/030631

U.S. Pat. No. 6,750,048, US 2011/295028, US 2015/176042, US 2014/350222

Fedorova-Dahms I. & al., Safety evaluation of DHA-rich algal oil from Schizochytrium sp, Food and Chemical Toxicology, 2011, 49, 3310-3318

Folch J, et al., A simple method for the isolation and purification of total lipides from animal tissues. J Biol Chem. 1957 May; 226(1):497-509

Hamilton M. & al., Heterotrophic Production of Omega-3 Long-Chain Polyunsaturated Fatty Acids by Trophically Converted Marine Diatom Phaeodactylum tricornum, Marine Drugs, 2016, 14, 53

Omega-3 long chain fatty acid "bioavailability": a review of evidence and methodological considerations. Ghasemifard S, Turchini G M, Sinclair A J. Prog Lipid Res. 2014 October; 56:92-108. doi: 10.1016/j.plip-res.2014.09.001. Epub 2014 Sep. 16. Review.

Wakako TSUZUKI, Study of the Formation of trans Fatty Acids in Model Oils (triacylglycerols) and Edible Oils during the Heating Process, JARQ 46 (3), 215-220 (2012)

Kinuko Miyazaki* and Kazuo Koyama, An Improved Enzymatic Indirect Method for Simultaneous Determinations of 3-MCPD Esters and Glycidyl Esters in Fish Oils, J. Oleo Sci. 66, (10) 1085-1093 (2017)

Jouhet J., Marechal E., Bligny R., Joyard J., Block M. A. (2003). Transient increase of phosphatidylcholine in plant cells in response to phosphate deprivation. FEBS Lett. 544 63-68.

Maged P. Mansour, 1,* Pushkar Shrestha, 2 Srinivas Belide, 2 James R. Petrie, 2 Peter D. Nichols, 1 and Surinder P. Singh2 (2014). Characterization of Oilseed Lipids from "DHA-Producing Camelina sativa": A New Transformed Land Plant Containing Long-Chain Omega-3 Oils. Nutrients. 2014 February; 6(2): 776-789.

Ruiz-Lopez N, Haslam R P, Napier J A, Sayanova O (2014) Successful high-level accumulation of fish oil omega-3 long chain polyunsaturated fatty acids in a transgenic oilseed crop. Plant J. 77(2):198-208

Rosenthal A, Pyle D L, and Niranjan K (1996) Aqueous and enzymatic processes for edible oil extraction. Enzyme and Microbial Technology 19:402-420.

The invention claimed is:

1. A process for extracting a PUFA-rich oil from a biomass of an oil producing organism comprising said oil, the process comprising the steps:
    (a) of cell lysis of the said oil-producing organism biomass, and
    (b) of mechanical separation of the oil from the lysed biomass of step (a) and recovery of the crude oil, wherein the cell lysis (a) comprises two parts:
        (a1) a first part carried out at a first temperature, followed by
        (a2) a second part of continued lysis at a second temperature lower than the temperature of the first part, wherein the temperature of step (a2) of the second part of lysis is at least 10° C. lower than the temperature of the first part (a1).

2. The process according to claim 1, wherein the biomass of an oil producing organism is a biomass of PUFA-producing microorganisms.

3. The process according to claim 2, wherein the biomass is a suspension of microorganisms.

4. The process according to claim 1, wherein the oil produced by the producing organisms comprises more than 50% PUFA.

5. The process according to claim 1, wherein the PUFAs are selected from docosahexaenoic acid (DHA, C22:6n3), docosapentaenoic acid (DPA, C22:5n6), arachidonic acid (ARA, C20:4n6), eicosapentaenoic acid (EPA, C20:5n3) and mixtures thereof.

6. The process according to claim 1, wherein the step (a) of lysis is a mechanical lysis.

7. The process according to claim 1, wherein the step (a) of lysis is an enzymatic lysis.

8. The process according to claim 1, wherein the temperature of the first part (a1) of lysis is of at least 50° C. and below 95° C.

9. The process according to claim 8, wherein the temperature of the second part of lysis (a2) is less than or equal to 40° C.

10. The process according to claim 1, wherein the mechanical separation (b) of an oil from a lysed biomass is a continuous separation by centrifugal plate separator.

11. The process according to claim 1, wherein the process comprises a step (c) of refining the crude oil obtained in step (b).

12. The process according to claim 1, wherein the process comprises a step (d) of diluting the crude oil obtained in step (b) or diluting the refined oil obtained in step (c).

13. The process according to claim 2, wherein the PUFA-producing microorganisms are selected from filamentous fungi and protists.

14. A process for extracting a PUFA-rich oil from a biomass of PUFA-producing microorganisms comprising the steps of:
(a) cell lysis of the said biomass of PUFA-producing microorganisms, and
(b) of mechanical separation of the oil from the lysed biomass of step (a) and recovery of the crude oil,
(c) of refining the crude oil obtained in step (b), and
(d) of diluting the crude oil obtained in step (b),
wherein the cell lysis (a) comprises two parts:
(a1) a first part carried out at a first temperature, followed by
(a2) a second part of continued lysis at a second temperature lower than the temperature of the first part,
and wherein the temperature of step (a2) of the second part of lysis is at least 10° C. lower than the temperature of the first part (a1).

15. The process according to claim 14, wherein the PUFA-producing microorganisms are selected from thraustochytrids, Dinophyceae, diatoms and Eustigmatophyceae.

16. The process according to claim 14, wherein the PUFA-producing microorganisms are DHA (docosahexaenoic acid) producing microorganisms selected from the genera *Crypthecodinium, Schizochytrium, Thraustochytrium* and *Aurantiochytrium*.

17. The process according to claim 14, wherein the PUFA-producing microorganisms are ARA (arachidonic acid) producing microorganisms selected from *Mortierella alpine, Mortierella elongata, Mortierella exigua, Mortierella hygrophila* and *Nannochloropsis gaditana*.

18. The process according to claim 14, wherein the PUFA-producing microorganisms are EPA (eicosapentaenoic acid) producing microorganisms selected from *Nannochloropsis gaditana, Phaeodactylum tricornutum, Nitzschia brevirostris, Nitzschia laevis, Pythium irregulare, Nannochloropsis limnetica, Nannochloropsis salina, Nannochloropsis avicula, Nannochloropsis acceptata, Nannochloropsis oculate, Nannochloropsis pseudotenelloides, Nannochloropsis* sp., *Nannochloropsis saprophila; Chlorella protothecoides, Chlorella ellipsoidea, Chlorella minutissima, Chlorella zofinienesi, Chlorella luteoviridis, Chlorella kessleri, Chlorella sorokiniana, Chlorella fiusca* var. *vacuolate, Chlorella* sp., *Chlorella emersonii*; and *Monodus subterraneus*.

* * * * *